United States Patent [19]
Daniele et al.

[11] Patent Number: 5,695,138
[45] Date of Patent: Dec. 9, 1997

[54] WINDING FIXTURE FOR SURGICAL SUTURE PACKAGE

[75] Inventors: Robert A. Daniele, Flemington; Anthony Esteves, Somerville; David Demarest, Parsippany, all of N.J.

[73] Assignee: Ethicon, Inc., Somerville, N.J.

[21] Appl. No.: 697,940

[22] Filed: Sep. 3, 1996

[51] Int. Cl.⁶ ............................ B65H 54/68; B65H 54/56; B65H 51/015
[52] U.S. Cl. ............................ 242/50; 242/53; 242/159
[58] Field of Search ............................ 242/47, 50, 53, 242/159, 899

[56] References Cited

U.S. PATENT DOCUMENTS

| | | | |
|---|---|---|---|
| 980,682 | 1/1911 | Saracco | 242/53 |
| 1,993,970 | 3/1935 | MacMurray | 242/50 |
| 2,727,699 | 12/1955 | Bilane et al. | 242/50 |
| 3,049,230 | 8/1962 | Van Scoy | 242/53 X |
| 5,165,217 | 11/1992 | Sobel et al. | 242/159 X |

*Primary Examiner*—Michael Mansen
*Attorney, Agent, or Firm*—Emil Richard Skula

[57] ABSTRACT

A suture winding fixture has a base plate. Fixedly mounted perpendicular to the base plate is a pivot shaft. Rotatably mounted to the pivot shaft is a cam housing frame member. A first opposed cavity in the frame member has a first cam shaft and first set of cams. A second opposed cavity Each cam shaft is rotatably mounted to the frame within the cavities. The frame also has a central cavity for receiving the pivot shaft. Fixedly mounted to the top of the pivot shaft in the central cavity is a pinion gear. The pinion gear engages a pair of opposed bevel gears, wherein each opposed bevel gear is mounted to an end of a cam shaft. Mounted to the top of the housing frame member is a package support member containing a plurality of winding pin holes. The package support member is shaped to conform to the dimensions of a suture winding tray having a top surface with a winding channel in which it is desired to load or wind a suture. Winding pins are mounted to a plurality of nested concentric cage plate members movably mounted on top of the frame. The nested cage plate members are sequentially engaged on their bottom sides by cam followers which are in turn engaged by the cams. Mounted to the top of the winding fixture after a package tray has been placed upon the package support member is a winding funnel member.

11 Claims, 16 Drawing Sheets

5,695,138

WINDING FIXTURE FOR SURGICAL SUTURE PACKAGE

TECHNICAL FIELD

The field of art to which this invention relates is mechanical winding fixtures, in particular, mechanical winding fixtures for surgical suture packages.

BACKGROUND OF THE INVENTION

Packages for surgical sutures are well known in the art. It is important that the packages protect the sutures from damage and shifting during shipping, handling, and storage. In response to these requirements, suture packages having winding channels have been developed. These packages may have, for example, oval-shaped winding channels for containing surgical sutures, along with needle parks for retaining surgical needles mounted to the sutures. It is known that these suture channel packages have advantages over other conventional suture package configurations in that the sutures and needles are easily withdrawn from the packages, the sutures tend not to take a set or memory when stored in these packages for long periods of time, and the packages are relatively easy to wind or load. Suture tray packages having winding channels are disclosed in U.S. Pat. Nos. 4,967,902; 5,052,551; 4,961,498; 5,131,533; and 5,213,210 which are incorporated by reference.

Even though the conventional suture channel packages have many advantages over other types of conventional suture packages, there is a constant need in the art for improvements. To this end, a suture package having a grooved winding surface was developed and is disclosed in commonly assigned, co-pending U.S. patent application Ser. No. 08/494,647 which is incorporated by reference. That novel package, which has a grooved winding surface requires a special winding apparatus to isolate or place individual coils of suture into the appropriate individual grooved sections of the winding channel.

Accordingly, there is a need in this art for a suture winding apparatus, which can be utilized in a mechanized suture winding operation, to wind suture into suture packages having a grooved winding surface.

DISCLOSURE OF THE INVENTION

Therefore it is an object of the present invention to provide a winding fixture which can be used to wind a suture into a tray-type suture package having a grooved winding surface channel for receiving a surgical suture such that the coils of suture are separated, preferably in individual grooves.

It is a further object of the present invention to provide such a suture winding apparatus which may be utilized in a high speed, automated suture winding operation.

It is a further object of the present invention to provide a suture winding fixture for a grooved suture winding tray which is economical to manufacture and use.

Accordingly, a suture winding apparatus is disclosed. The suture winding apparatus has a base plate. Mounted perpendicularly to the base plate is a pivot shaft. The pivot shaft is fixedly mounted to the base plate. Rotatably mounted to the pivot shaft is a cam housing frame member. A first opposed cavity has a first camshaft and first set of cams. A second opposed cavity has a second cam shaft and a second set of cams. Each cam shaft is rotatably mounted to the frame within the cavities. The frame also has a central cavity for receiving the pivot shaft. Fixedly mounted to the top of the pivot shaft in the central cavity is a pinion gear. The pinion gear engages a pair of opposed bevel gears, wherein each opposed bevel gear is mounted to an inner end of a cam shaft. Mounted over the top of the housing frame member is a package support member containing a plurality of winding pin holes. The package support member is mounted such that there is a cavity between the bottom of the package support member and the top of the frame. The package support member is shaped to conform to the dimensions of a suture winding tray having a grooved surface in which it is desired to load or wind a suture. The top of the package support member has a pair of opposed pilot pin members extending upwardly. The top of the cam housing frame member also has a plurality of vertical slots contained therein for receiving a plurality of movable cam followers. The winding pins are mounted to a plurality of nested concentric cage plate members movably mounted on top of the frame. The nested cage plate members are sequentially engaged on their bottom sides by cam followers. Mounted to the top of the winding fixture after a package tray has been placed upon the package support member is a winding funnel member. The winding funnel member has a plurality of winding pin holes for receiving winding pins as well as at least two pilot alignment pin holes for receiving pilot alignment pins, and also has a lower beveled suture engagement surface. As the winding fixture cam housing is rotated with respect to the base plate, the bevel gears are caused to rotate thereby rotating the cams and the cam shafts and sequentially engaging nested cage plate members thereby sequentially extending a plurality of winding pins such that as a surgical suture is wound in a package tray, the suture is guided into the grooves of the winding tray beginning with the inner grooves and ending with the tail of the suture in the outer groove.

Yet another aspect of the present invention is a method of winding a surgical suture into a surgical suture tray package having a grooved winding channel using the winding fixture apparatus of the present invention.

The foregoing other features and advantages of the present invention will become more apparent from the following description and the accompanying drawings.

DESCRIPTION OF THE PREFERRED EMBODIMENTS

Figure 5:
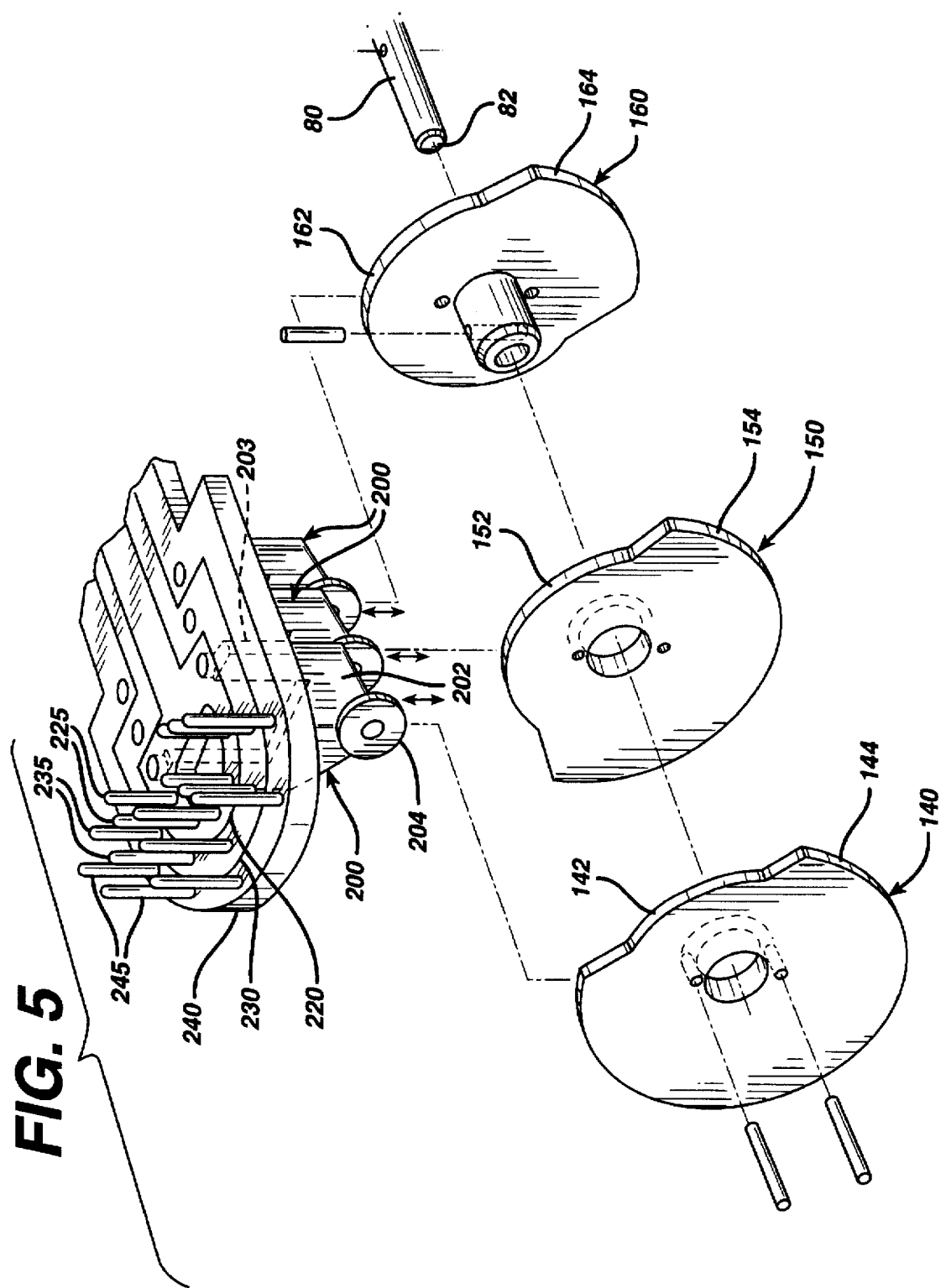
FIG. 5 is a partial, exploded perspective view of the apparatus of FIG. 2 illustrating one set of cams used to raise and lower the cage plates and winding pins.

Referring initially to FIGS. 1, 2, 3 and 4, the winding fixture 10 of the present invention is seen to be illustrated. The winding fixture 10 is seen to have a base plate 20. The base plate 20 is seen to be substantially rectangular in shape, however, any geometric shape can be utilized including circular, oval, rectangular, polygonal, etc., and combinations thereof. The base plate 20 has top 22 and bottom 24. The pivot shaft 30 is seen to be mounted perpendicularly to the base plate 20. Pivot shaft 30 is seen to have bottom 32 and top 34. Pivot shaft 30 is, preferably, fixedly mounted to the base plate 20, however, in an alternate embodiment, the shaft 30 may be rotatably mounted to base plate 20. Concentrically mounted to the bottom 32 of the pivot shaft 30 is the bushing 40. The bushing 40 is seen to rest on top of the top 22 of the base plate 20. Rotatably mounted to the pivot shaft 30 and the bushing 40 is the cam frame housing 50. Cam frame 50 is seen to have central opening 51 for receiving pivot shaft 30 and bushing 40. Extending through the bottom of frame 50 is the bottom 34 of shaft 30. The cam frame housing 50 is also seen to have first and second cavities 60 and 70. Mounted transversely in the cavities 60 and 70 are the first and second cam shafts 80 and 90 respectively. The first end 82 of cam shaft 80 is seen to be mounted to bushing 89 contained in side 61 of housing 50. The second end 83 of cam shaft 80 is seen to be mounted in bushing 88 in side 65 of housing 50. Mounted to cam shaft 80 is the outer cam 140, the middle cam 150 and the inner cam 160. Referring also to FIG. 5, cam 140 is seen to have dwell section 142 and engagement section 144. Cam 150 is seen to have dwell section 152 and engagement section 154. Cam 160 is seen to have dwell section 162 and engagement section 164.

The first end 92 of second cam shaft 90 is seen to be mounted to bushing 98 contained in side 67 of housing 50. The second end 93 of cam shaft 90 is seen to be mounted in bushing 99 in side 68 of housing 50. Mounted to the cam shaft 90 is the outer cam 170, the middle cam 180 and the inner cam 190. Cam 170 is seen to have dwell section 172 and engagement section 174. Cam 180 is seen to have dwell section 182 and engagement section 184. Cam 190 is seen to have dwell section 192 and engagement section 194.

Contained in the top 55 of frame 50 are the cam follower holes 57. Mounted in the cam follower holes 57 are the cam followers 200. Referring to FIGS. 5, 7, 9 and 10, cam followers 190 are seen to have bottom section 202, legs 203, and protruding roller member 204 conventionally mounted to bottom section 202. There is one cam follower mounted in a follower hole 57 for each cam. The ends 204 of the legs of the cam followers 200 are seen to be welded to nest members which are further described below. If desired, although not preferred, roller member 204 can be replaced by a nonmoving protuberance extending from bottom section 202. Mounted to the ends 83 and 93 of the cam shafts 80 and 90, respectively, are the bevel gears 100 and 110. The ends 83 and 93 are seen to extend through walls 65 and 67, respectively, of frame 50. Bevel gears 100 and 110 are seen to engage the pinion gear 130 which is mounted to the top end 34 of shaft 30 by set screw 131 or equivalent fastening means.

Figure 13:
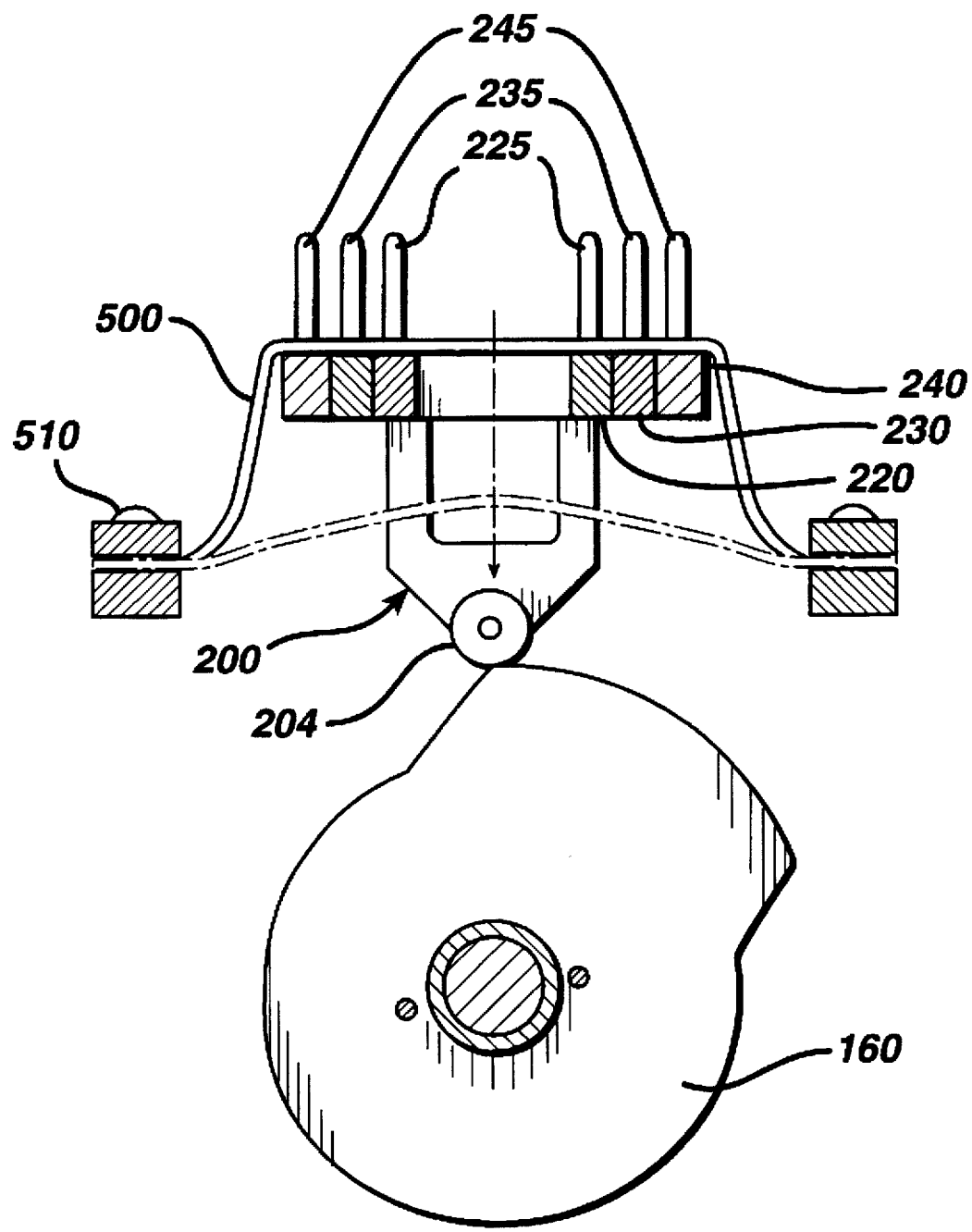
FIG. 13 illustrates a partial cutaway side view of the winding apparatus of the present invention illustrating all of the nested cage plates in a fully extended position.

The package support 210 is seen to be mounted to the top of frame 50 by the support brackets 215. Screws 216 are utilized to secure brackets 215 to the top of frame 50. Package support 210 is seen to have winding pin holes 217 extending therethrough. The package support 210 is seen to have a generally oval shape. In addition, the pilot alignment pins 218 and 219 are seen to extend upwardly from the top 211 of package support 210. Mounted beneath the bottom of package support 210 and on the top 55 of the frame 50 are the concentric nested cage members 220, 230 and 240. The nested cage plate members are seen to be substantially oval shaped members having hollow interiors. Concentric nested cage plate member 220 is the innermost nested cage plate member and is seen to have upwardly extending winding pins 225 mounted thereto. Concentric nested cage plate member 240 is seen to be the outermost nested cage plate member and is seen to have winding pins 245 mounted thereto and extending upwardly. Sandwiched between inner concentric nested cage plate member 220 and outer concentric nested cage plate member 240 is the intermediate concentric nested cage plate member 230 having upwardly extending winding pins 235 mounted thereto. As seen in FIG. 13, it is preferred to have optional biasing member 500 mounted to the top of frame 50 by fasteners 510 to provide a downward biasing force on the concentric nest members 230, 240 and 250. The biasing force assures that the cam followers will maintain good contact with the surfaces of the cams and also serves to assist in lowering the cage plate members when the cams are in the dwell positions. Preferably one biasing member 500 will be mounted on each end of frame 50 over the top of the first and second cavities 60 and 70, respectively.

Figure 1:
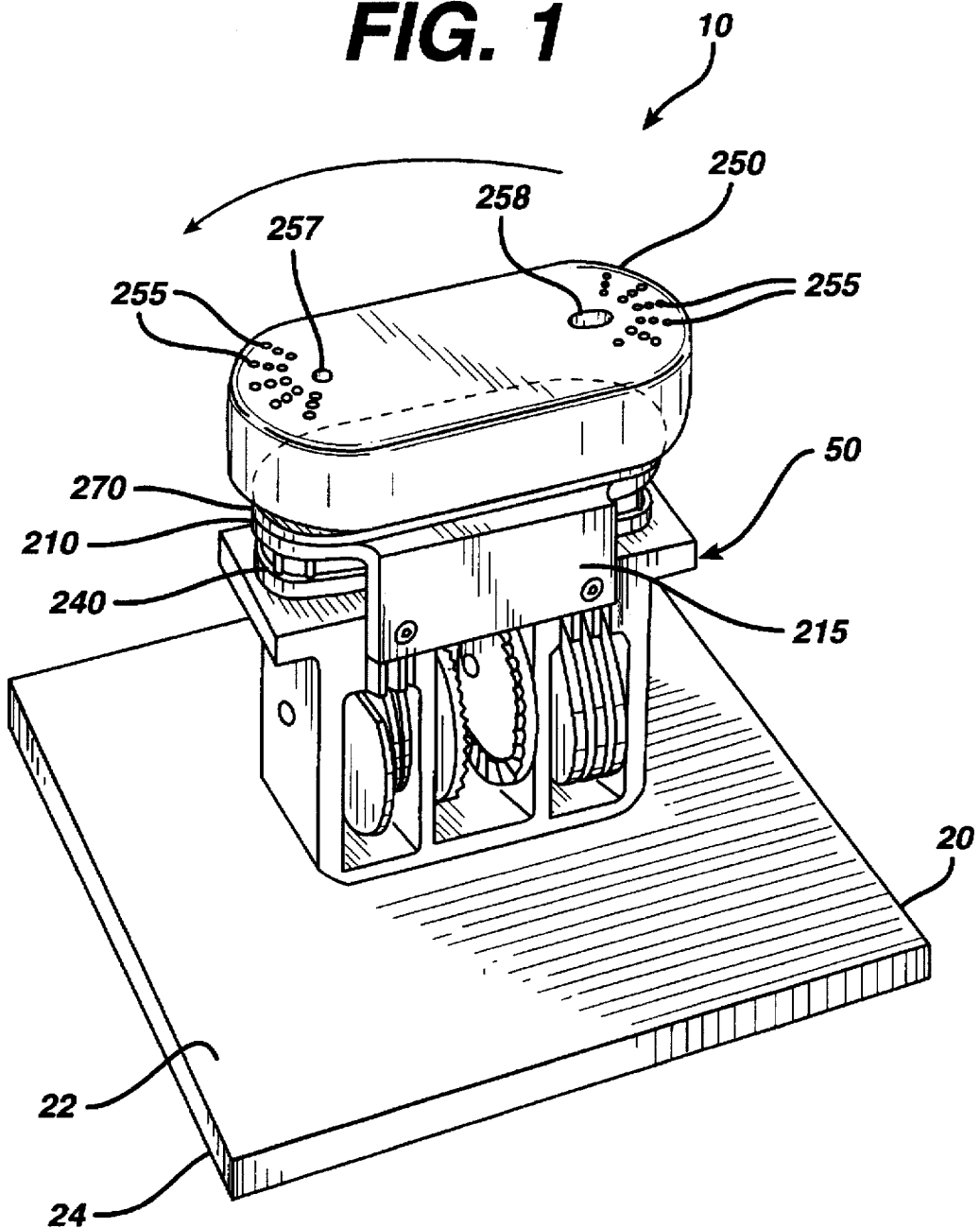
FIG. 1 is a perspective view of the winding fixture of the present invention.
Figure 2:
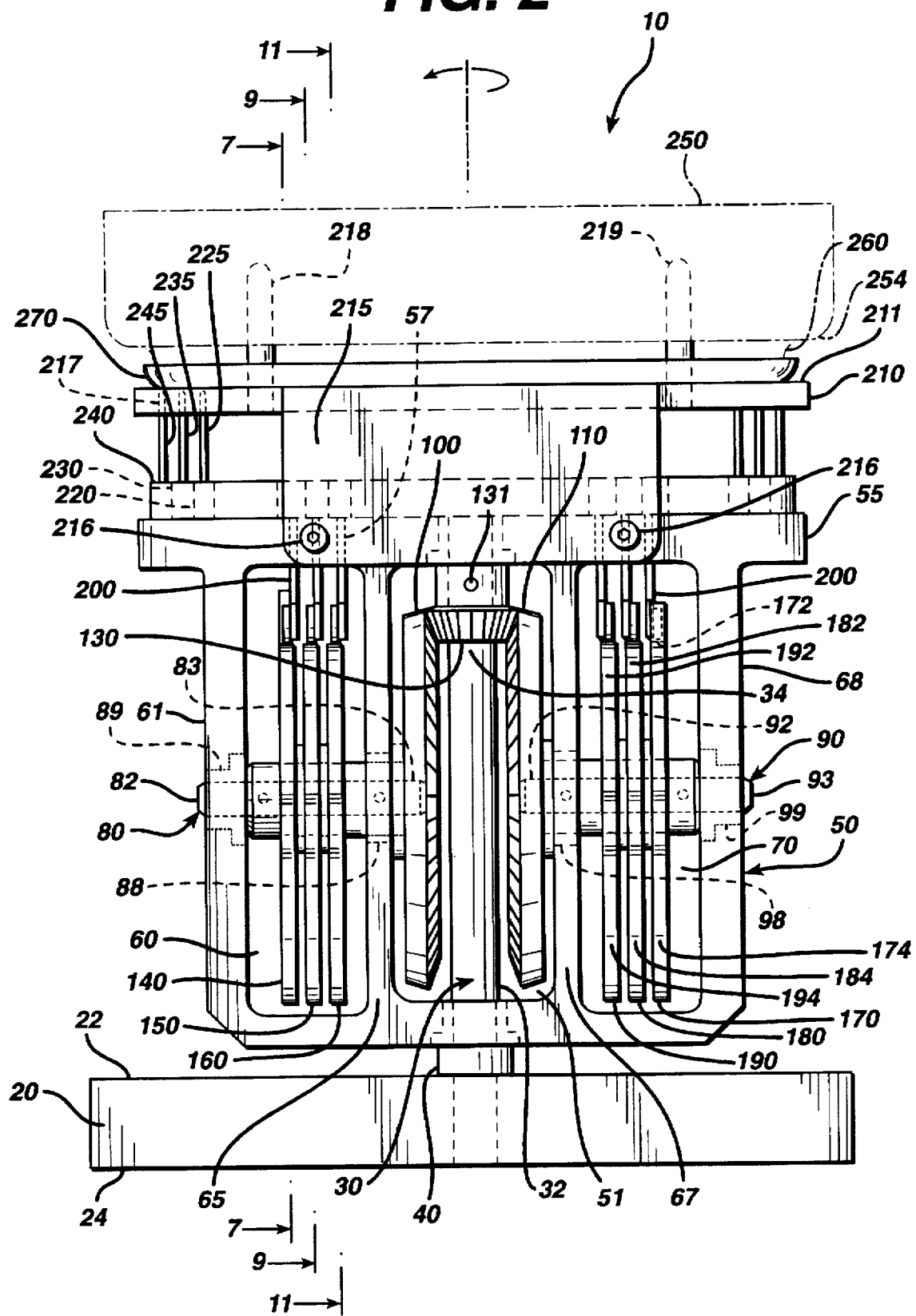
FIG. 2 is a front view of the winding fixture of the present invention.
Figure 3:
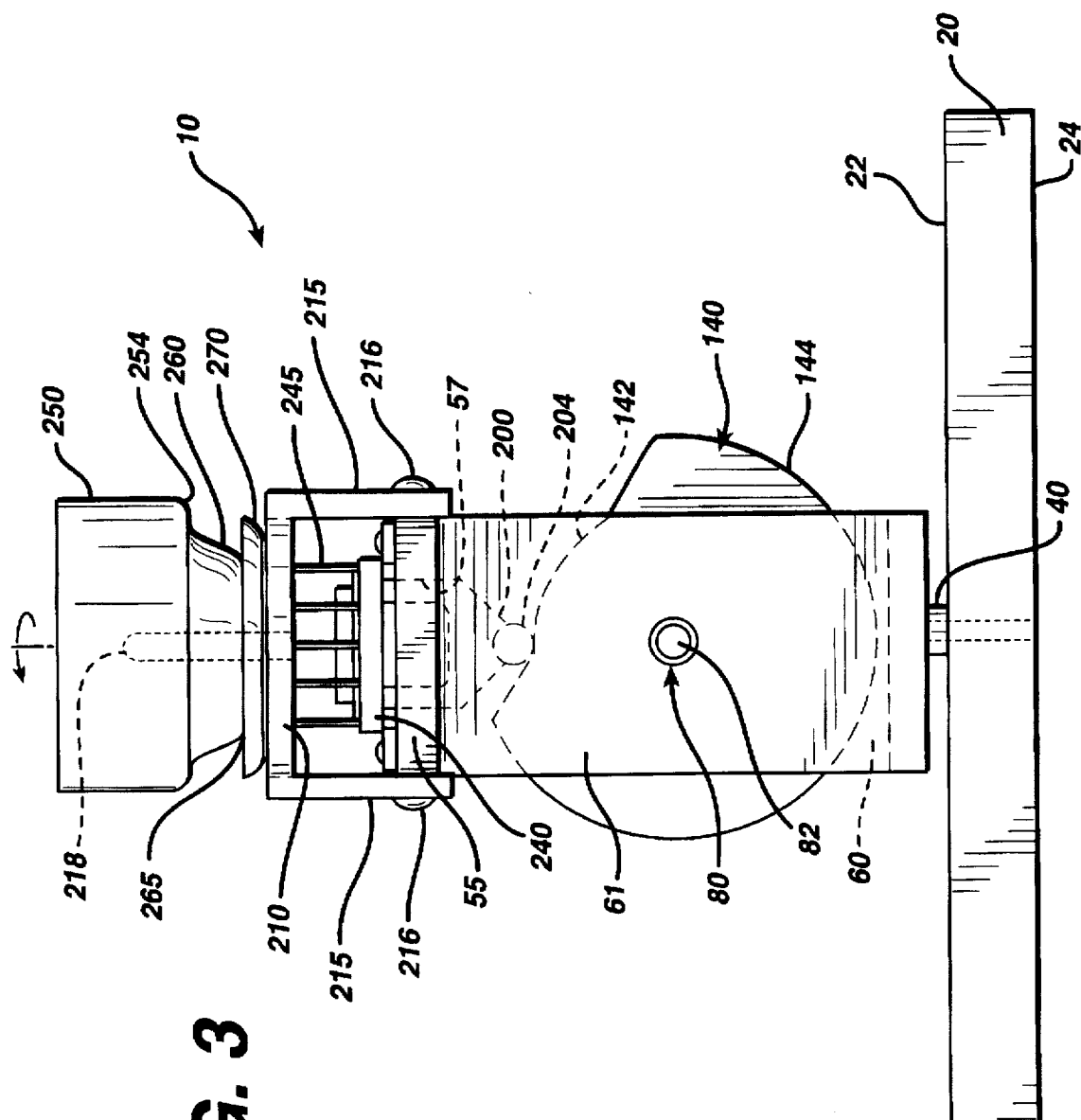
FIG. 3 is a side view of the winding fixture of the present invention.
Figure 4:
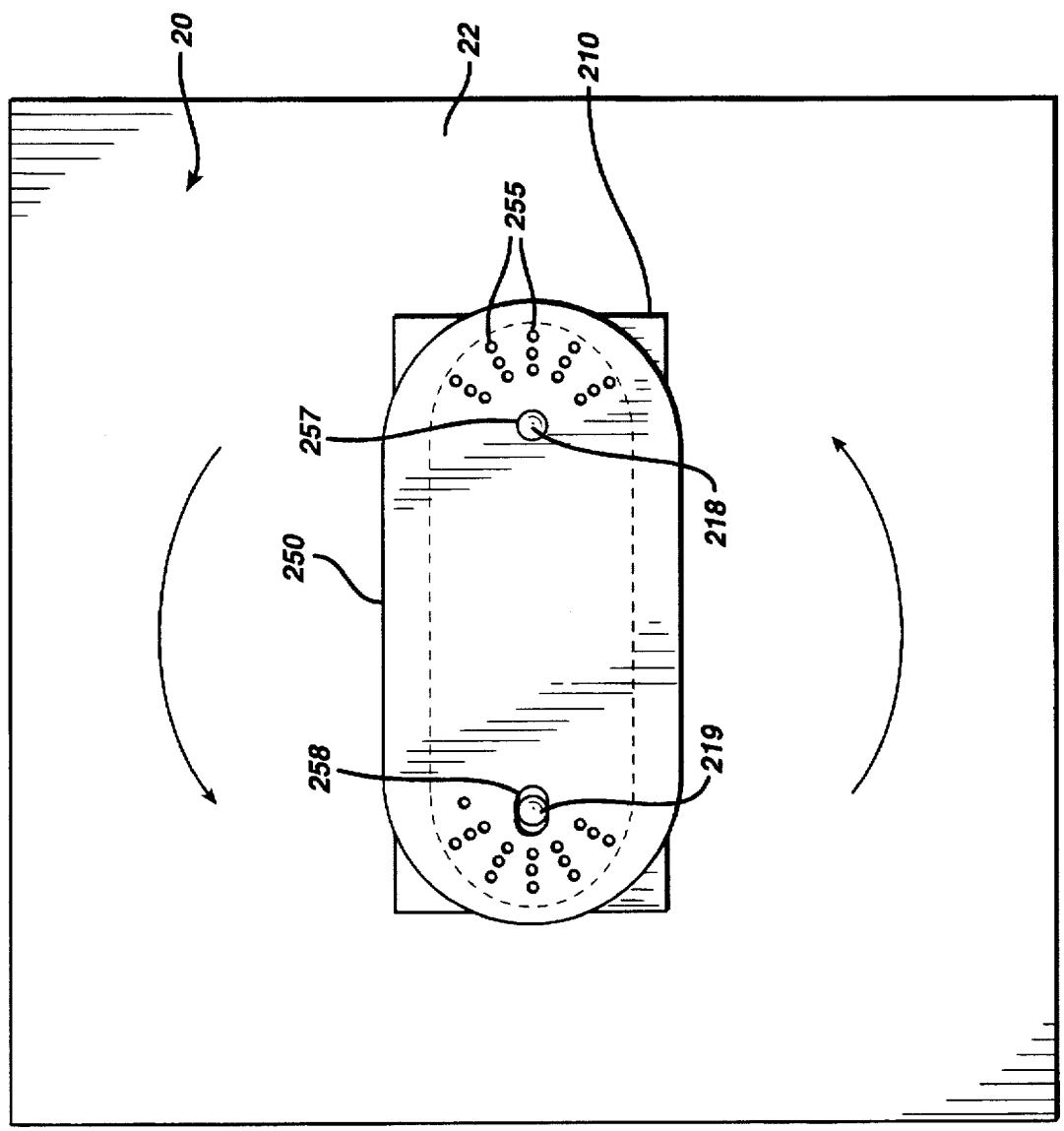
FIG. 4 is a top view of the winding fixture of the present invention.
Figure 6:
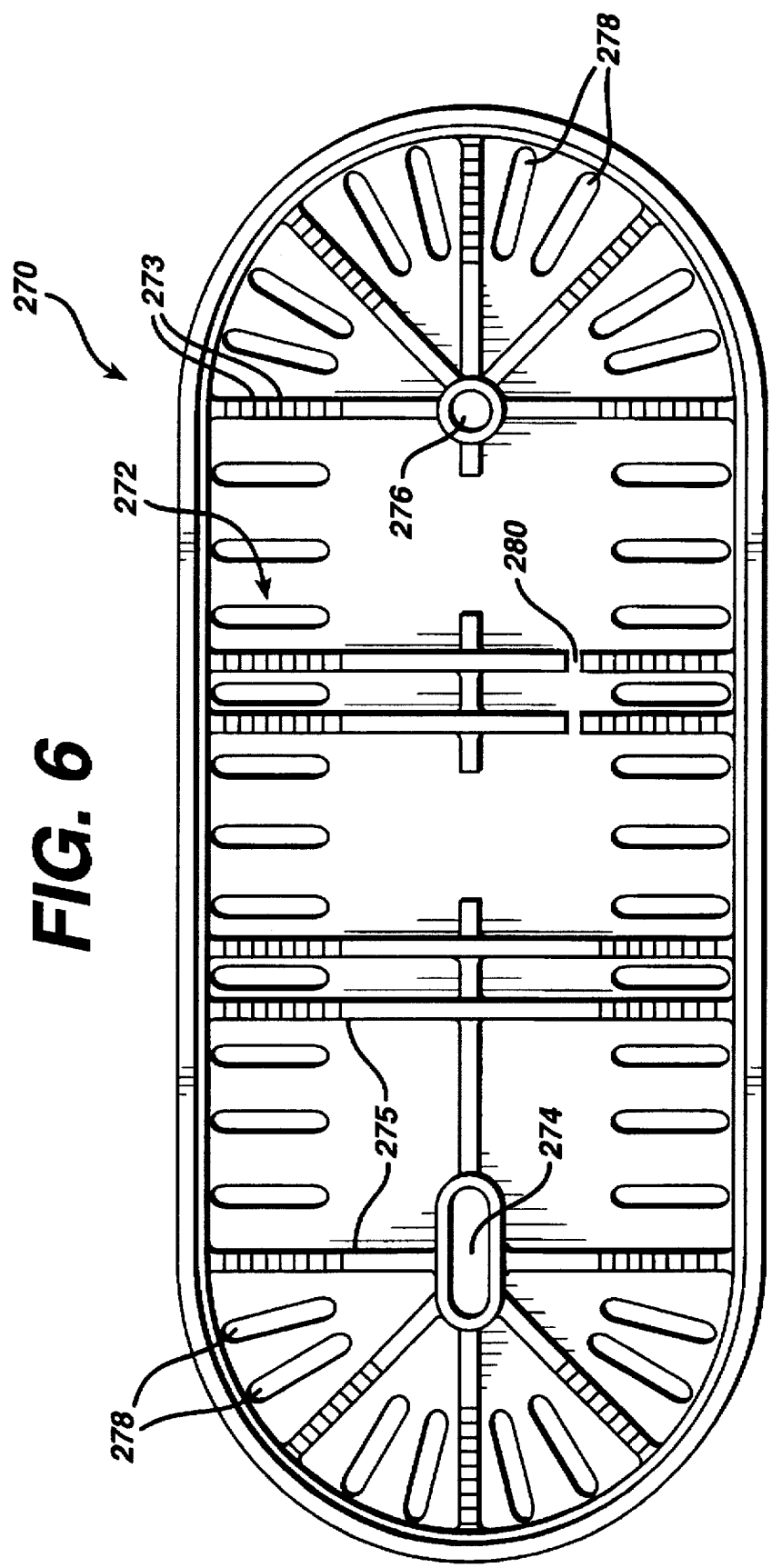
FIG. 6 is a top view of an oval package of the present invention having a grooved oval winding channel.
Figure 8:
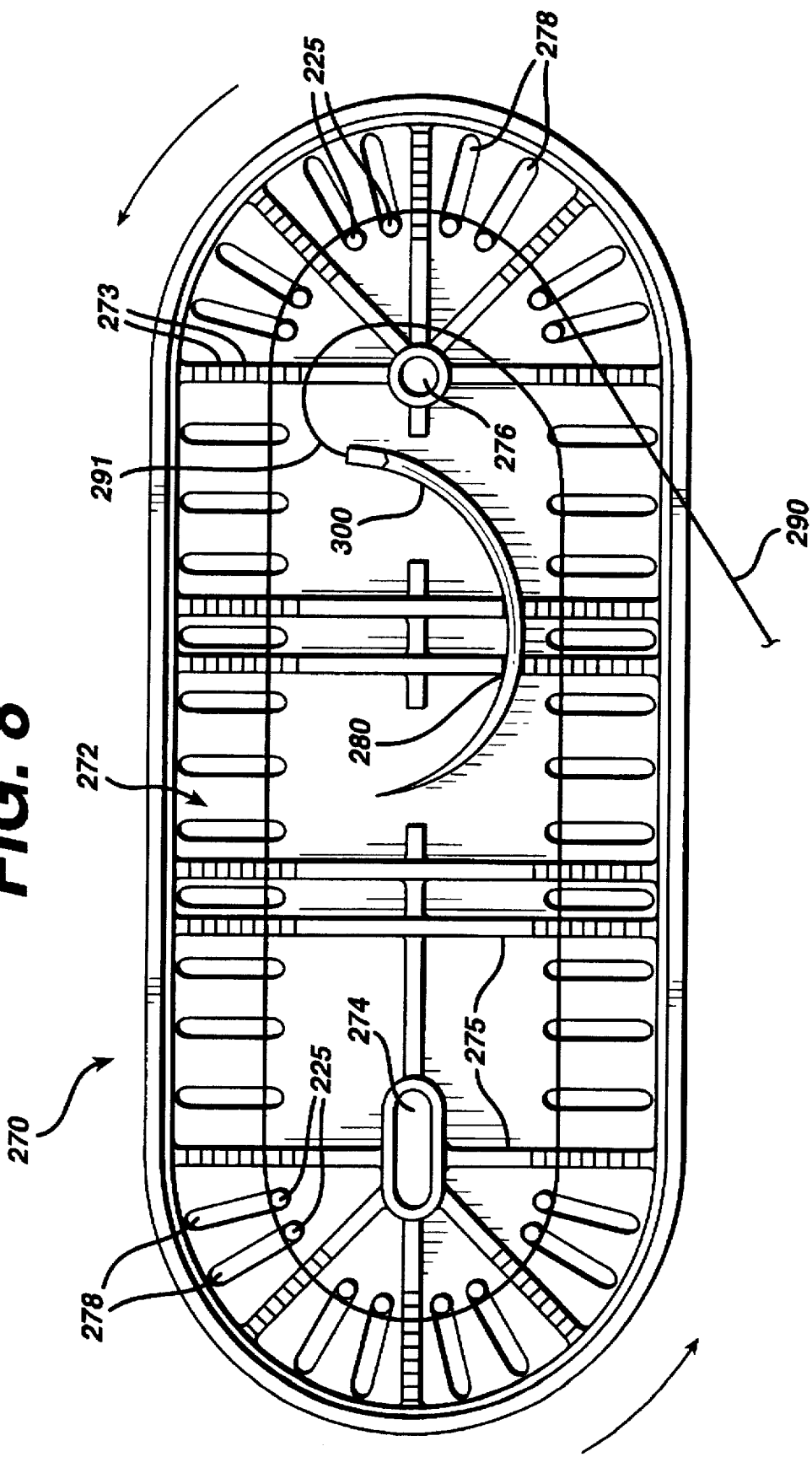
FIG. 8 is a top view of the suture tray of FIG. 6 showing the initial coil of suture being wound around the initial set of winding pins.
Figure 10:
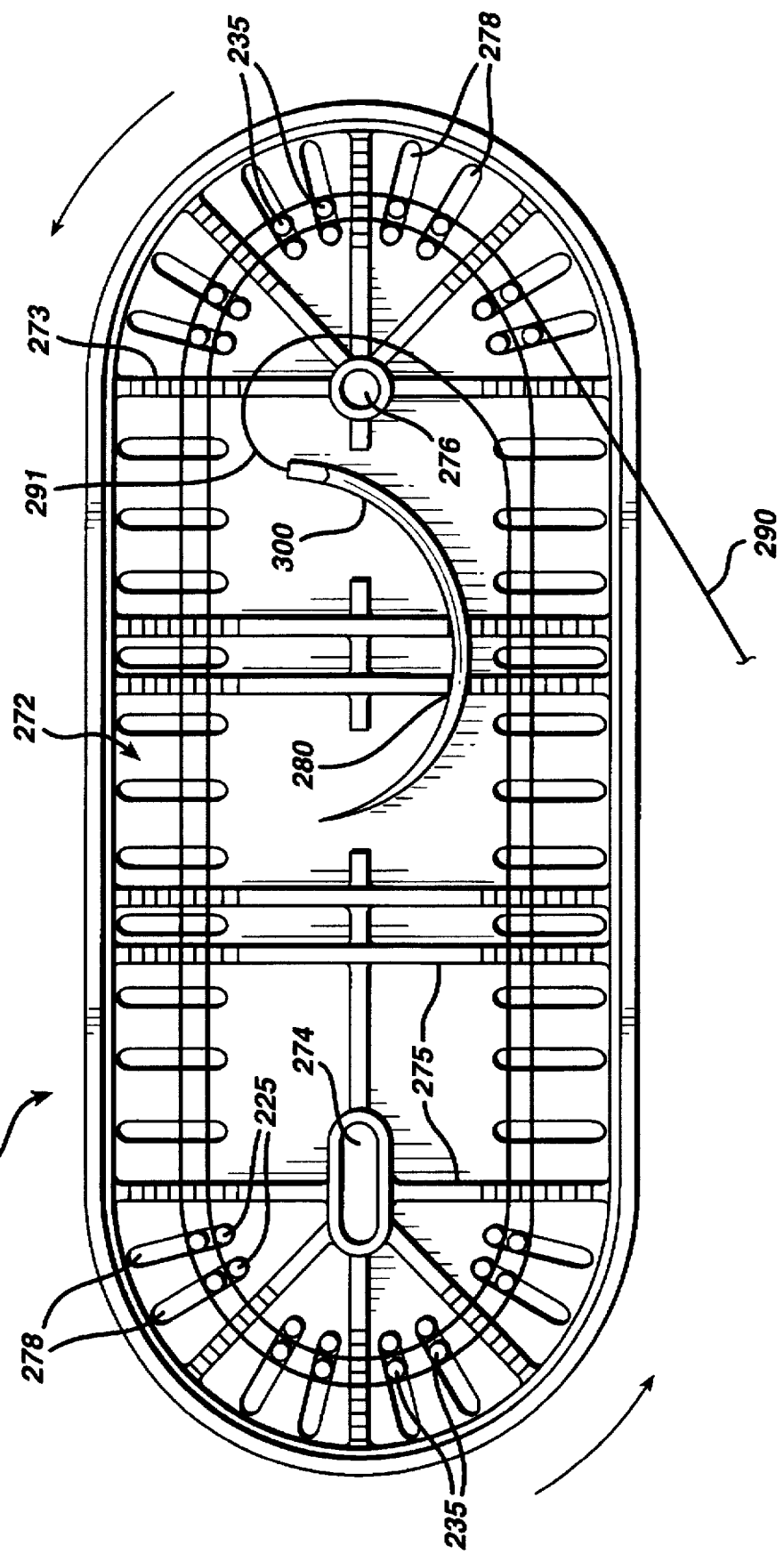
FIG. 10 is a top view of the suture package of FIG. 8 illustrating a second coil of suture being wound about a second set of winding pins.

Referring now to FIGS. 1, 2 and 3, a suture tray 270 having a grooved oval winding channel is seen to be mounted to the package support member 210 over the pilot pins 218 and 219. The tray 270 is illustrated in FIGS. 6, 8 and 10. The tray 270 is seen to have a winding channel 272, grooves 273, support members 275 and pilot holes 274 and 276. The tray 270 further is seen to have winding pin holes 278 in the channel 272 along with a conventional needle park 280. Mounted in the needle park 280 is a surgical needle 300 which is mounted to one end 291 of a surgical suture 290. Mounted to the package support 210 over the pilot pins 218 and 219 and on top of the tray 270 is the winding funnel 250. The winding funnel 250 is seen to have an outer periphery substantially similar in shape to the outer periphery of the tray 270. The winding funnel 250 is seen to have beveled bottom edge 254. In addition, winding funnel 250 is seen to have pilot holes 257 and 258 for accepting pilot pins 218 and 219 respectively, and additionally, to have pin holes 255 to accept winding pins 235, 225 and 245. The winding funnel 250 additionally is seen to have lower winding funnel surface 260 and bottom 265 which rests upon package 270 during the winding process.

Figure 7:
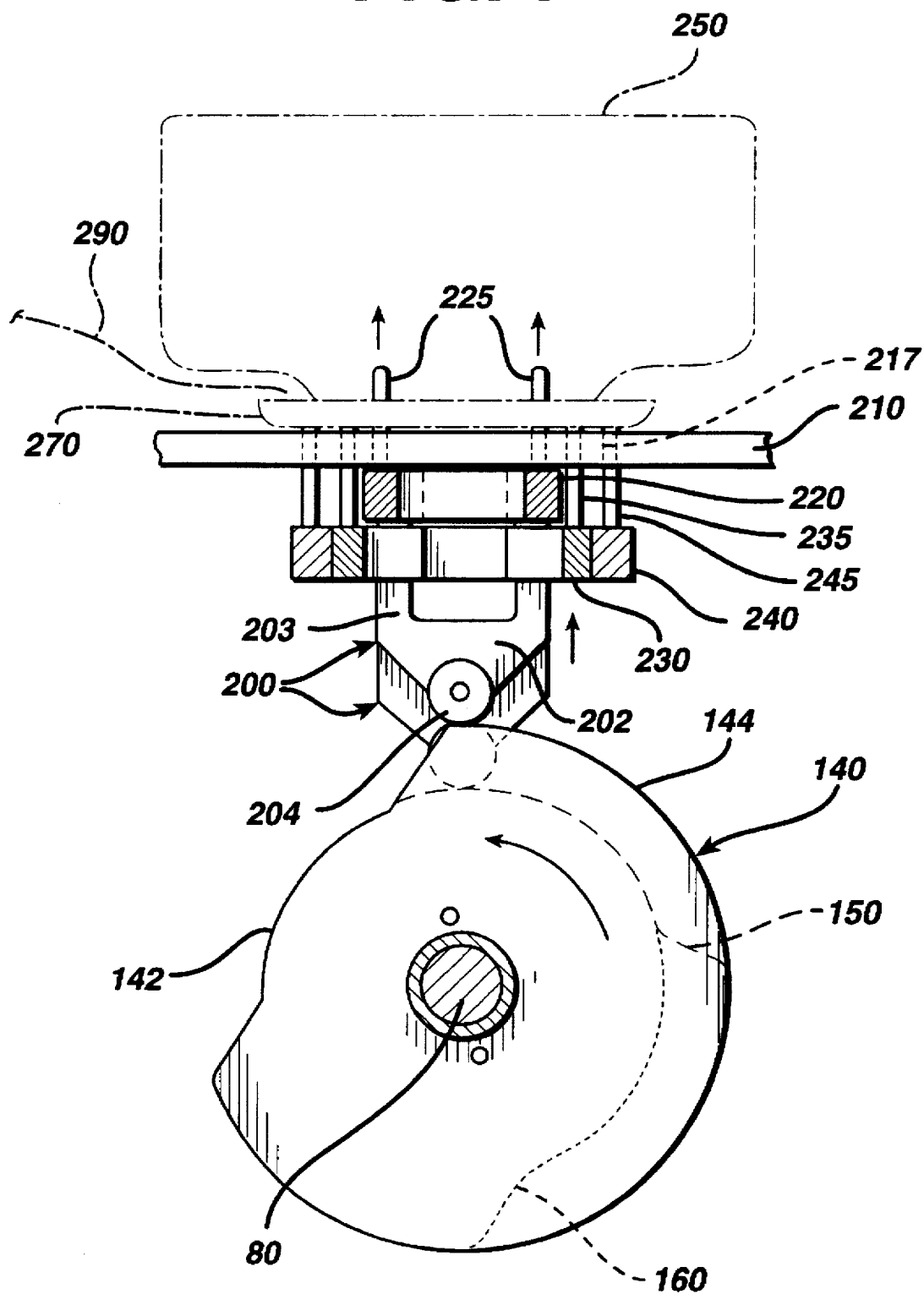
FIG. 7 is a partial cross-sectional, side view of the winding fixture of FIG. 2 showing the first or inner cam engaging the first cage plate thereby raising the winding pins through the bottom of the suture tray as seen along View Line 7—7.
Figure 9:
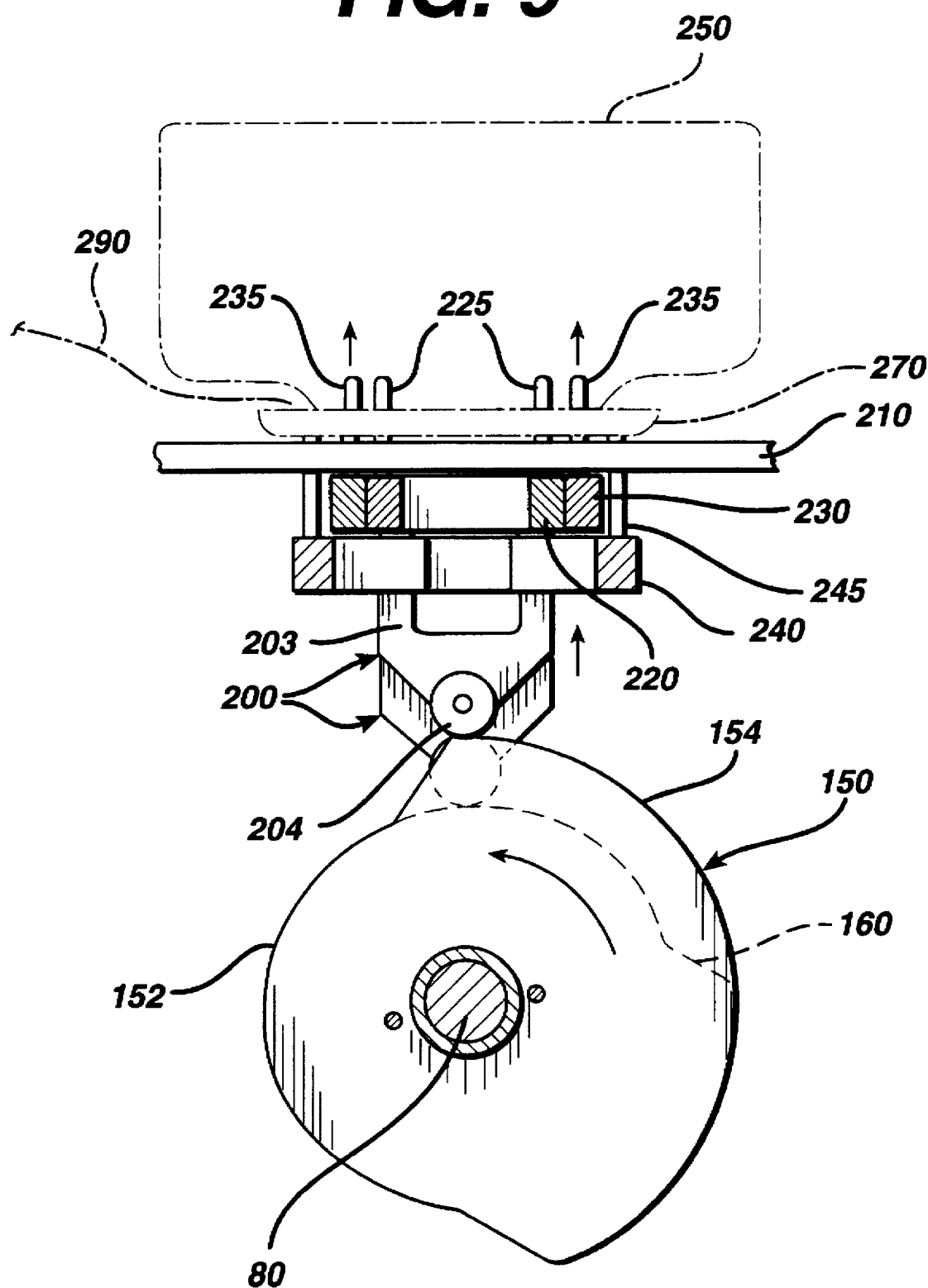
FIG. 9 is a cross-sectional, side view of the apparatus of FIG. 2 showing a second cam engaging the second cage plate thereby raising the second set of pins through the winding holes of the tray package, thereby permitting a second coil of suture to be wound in an arranged fashion as seen along View Line 9—9.
Figure 11:
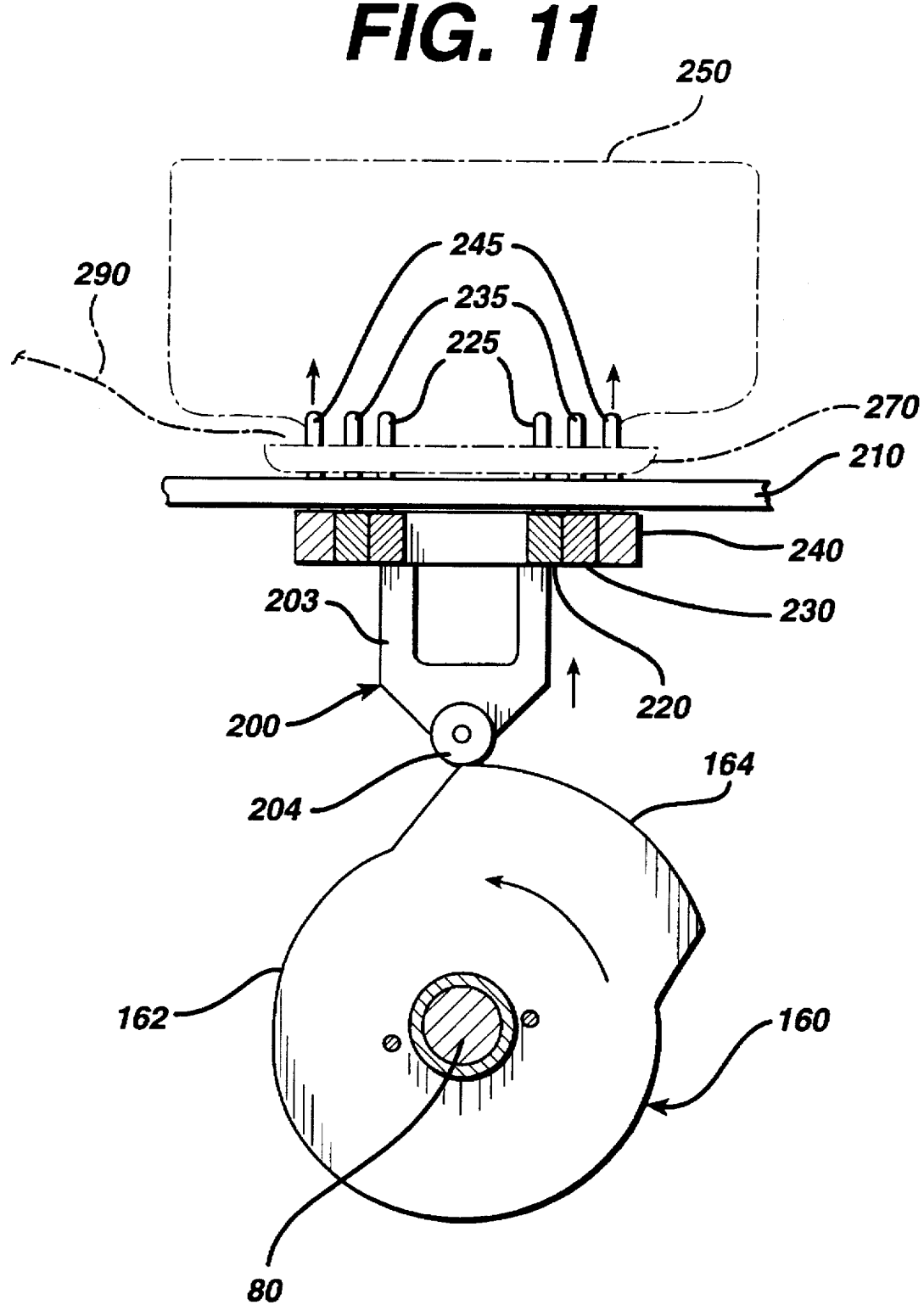
FIG. 11 is a partial, cross-sectional side view of the apparatus of FIG. 2 illustrating third or inner cam engaging a cam follower which in turn engages the outermost concentric cage plate thereby causing the third set of winding pins to be raised through the winding holes of the tray package as seen along View Line 11—11.
Figure 12:
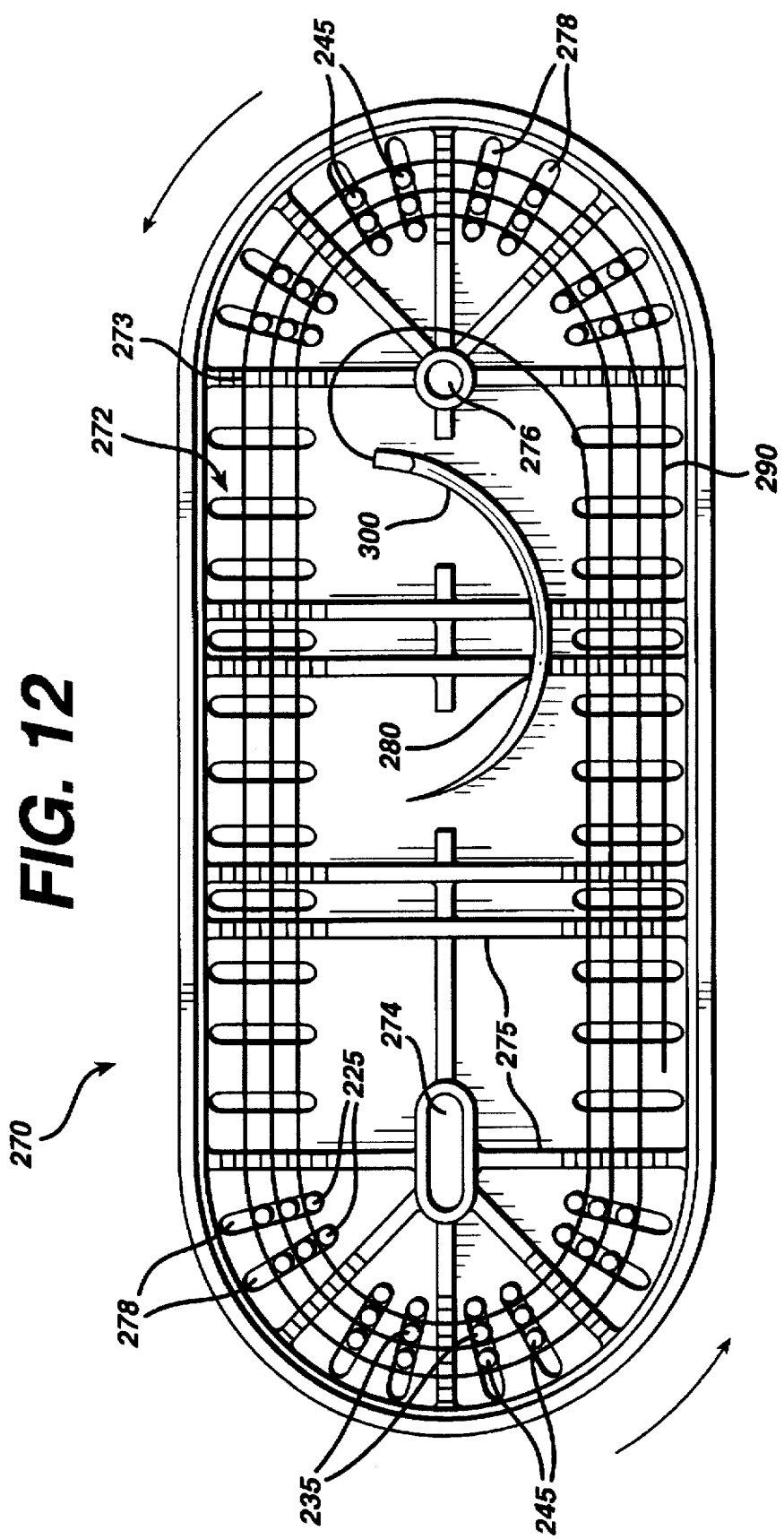
FIG. 12 illustrates the tray package of FIG. 10 after the winding process has been completed illustrating three coils of sutures arranged in an arranged wind pattern.

Referring now also to FIGS. 7, 9 and 11, the winding fixture apparatus 10 of the present invention is seen to operate in the following fashion. A suture package 270 is mounted to the top of the package support 210. A surgical needle 300 mounted to a suture 290 is mounted in needle park 280. Next the winding funnel 250 is placed on top of the package containing the surgical needle 300 and a section of suture 290 and engage pilot pins 218 and 219 in holes 257 and 258. The remainder of the suture 290 is loaded in the following manner. Rotating the frame 50 with respect to the base plate 20 about pivot shaft 30 causes the teeth of the bevel gears 100 and 110 to engage the pinion gear 130 thereby causing cam shafts 80 and 90 to rotate in opposite directions. Alternatively, if desired, base plate 50 may be rotated with respect to frame 50. During the initial rotation of frame 50, all of the cam followers are engaging the dwell sections of the cams. The suture 290 is wound around the winding funnel surface 260 during the initial rotation. During the second rotation, the engagement surfaces 162 and 192 of inner cams 160 and 190 engage a cam followers 200 thereby lifting the legs 203 of the cam followers 200 through the openings 57 in the frame 50. This causes the inner nested cage plate member 220 to raise and to, thereby, push the winding pins 225 through the pin holes 217 in the package support 210 and through the winding pin holes 278 in the package 270. The intermediate cams 150 and 180 and outer cams 140 and 170 at this point are in a dwell phase such that the cam followers are not moving upward to displace upwardly the intermediate and outer nest members 230 and 240, respectively. As the frame 50 rotates, the suture engages the winding pins 225 thereby causing the suture coils to be contained in grooves 273 of winding channel 272. After two complete revolution of frame 50 about shaft 30, the intermediate middle cams 150 and 170 move out of the dwell phase and enter the active or engagement phase thereby pushing up the respective cam followers 200 to in turn displace upwardly the intermediate nested cage plate member 230 and thrusting the winding pins 235 through the package support 215 and the holes 278 of package tray 270. At the beginning of the fourth rotation of frame 50 about shaft 30, the third outer nested cage plate member 240 is displaced upwardly by cam followers 200 which are activated by the outer cams 140 and 170 thereby thrusting the winding pins 245 through the package support 215 and the pin hole openings 217 in the package tray 210. After a complete fourth revolution, the suture is completely wound within the winding channel of the package and the fixture is further rotated until all the cams are in a dwell phase thereby causing the cam followers to move vertically downward and disengaging the winding pins 225, 235, and 245 from the package support 210 and the package 270 and causing the inner, intermediate and outer concentric nested cage plate members 220, 230, and 240, respectively, to rest upon the top 55 of the frame 50. The winding funnel 250 is then removed from the top of the package 270 and the package support 210 and then the package 270 containing the wound suture 290 and needle 300 is removed from the package support 210. The process is then repeated with an additional suture package tray 270 and needle 300 and suture 290.

It will be appreciated by those skilled in the art that the gear ratios of the bevel gears 100 are 110 and pinon gear 130, as well as the dwell and engagement surfaces of the cams 140, 150 and 160 will be selected to provide the desired gear ratios and dwell and engagement surfaces to translate the rotary motion of the frame 50 or shaft 30 into the desired rotary motion of the cam shafts 80 and 90, and to provide for the desired linear motion of the cam followers and nested cage plate members. For example in the embodiment illustrated in the Figures and described herein, one full turn of frame 50 is translated into a partial turn of shafts 80 and 90. In addition, the inner cams are seen to have longer engagement sections and shorter dwell sections than the outer cams. Gear ratios and dwell and engagement sections of cams will depend upon package configuration, the number of coils of suture desired to be wound, the number of nested cage plate members, etc.

Figure 14:
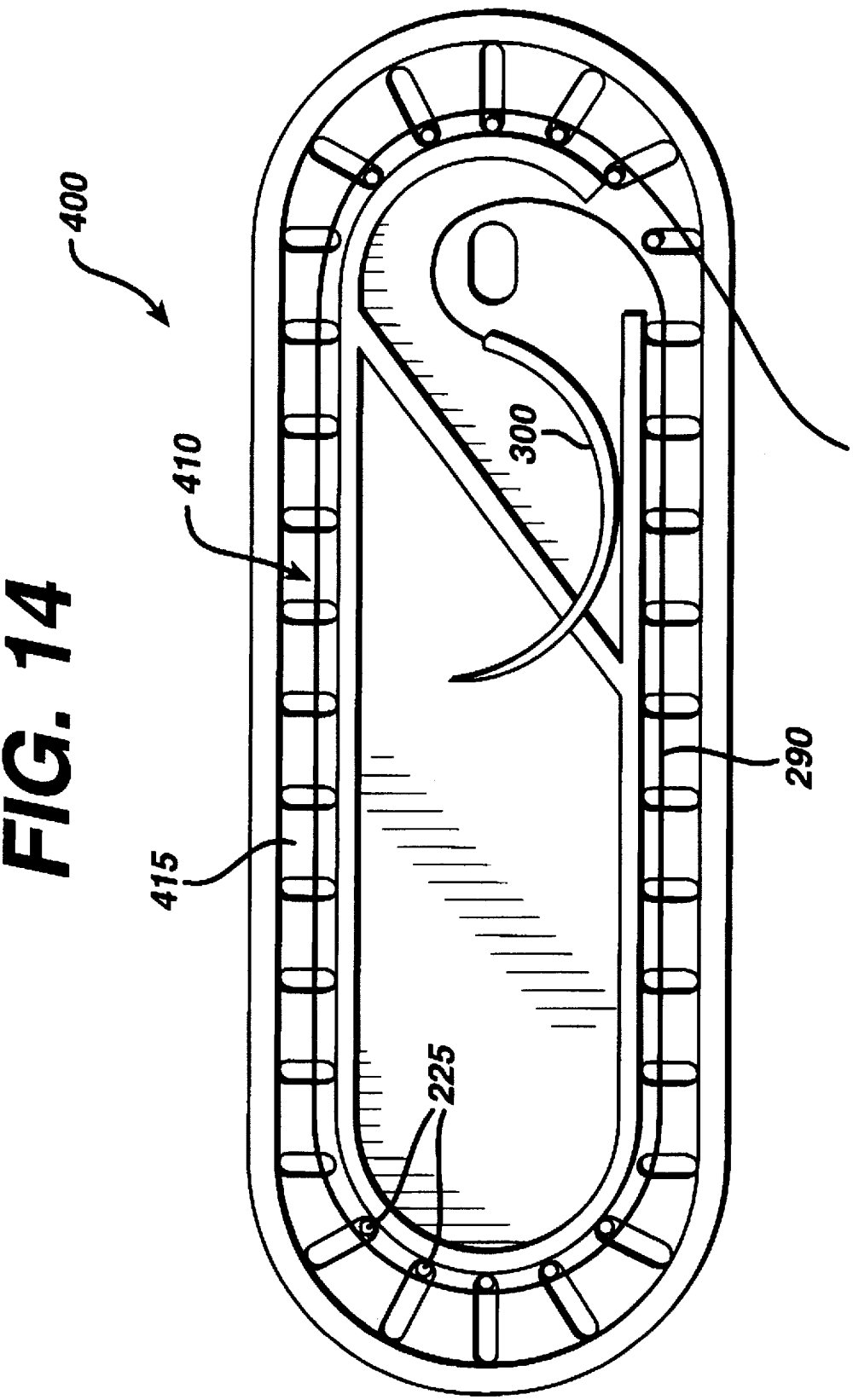
FIG. 14 is a top view of an oval suture tray package having an oval winding channel with a flat bottom showing an initial coil of suture being wound around the initial set of winding pins.
Figure 15:
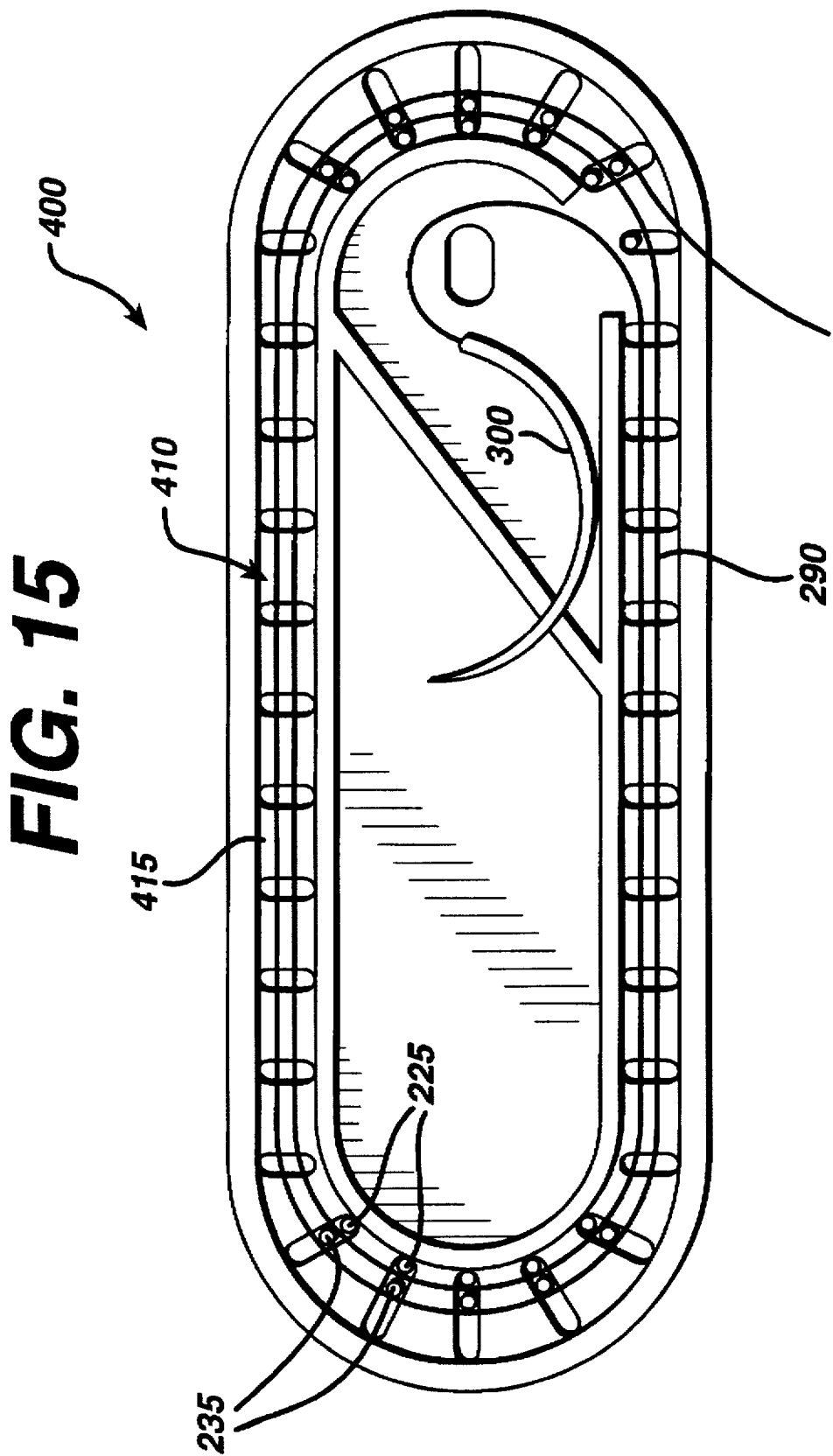
FIG. 15 is a top view of the suture tray of FIG. 14 showing a second coil of suture being wound around the second set of winding pins.
Figure 16:
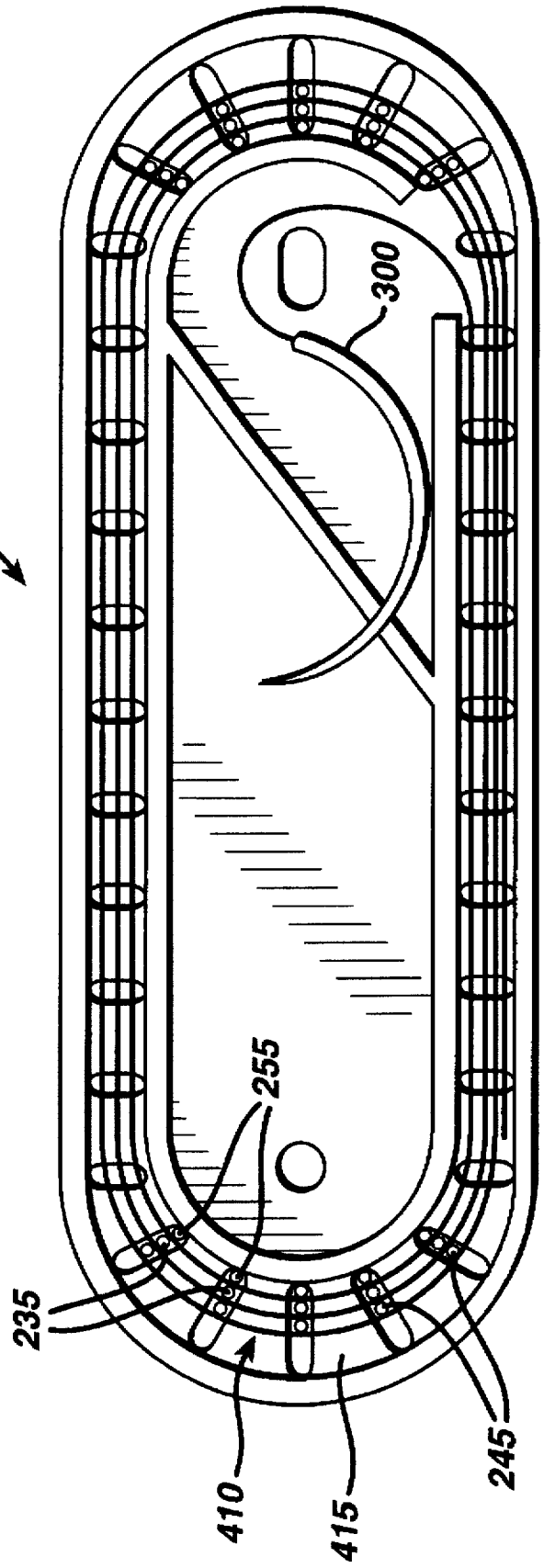
FIG. 16 illustrates the tray package of FIG. 15 after the winding process has been completed illustrating three coils of sutures arranged in an arranged wind pattern.

Another embodiment of a suture package which can be used with the winding fixture 10 of the present invention is seen in FIGS. 14, 15, and 16. The method of winding is similar to that described above. The package 400 is seen to have winding channel 410. Using the apparatus of the present invention, a suture 290 can be wound in channel 410 in an arranged wind pattern wherein no coils of suture cross over or under each other during the winding operation. Winding channel 410 does not have grooves, merely a flat bottom 415.

The winding fixture 10 of the present invention has many advantages. The fixture 10 may be rotated by hand or by a high speed motor in an automated suture package winding operation. The fixture 10 can be used to load grooved or conventional winding channels. The fixture 10 may be modified to load anywhere from one to ten or more coils of suture in a winding channel by correspondingly increasing the number of cams, cam followers, nest cage plate members and sending pin holes utilized. In addition, the use of gears and cams provides extremely precise winding of sutures in winding channels.

We claim:

1. A winding fixture for a surgical suture package comprising:

a base plate having a top and a bottom;

a pivot shaft fixedly mounted to the base plate;

a cam housing frame means rotatably mounted to the shaft;

cam means rotatably mounted in said cam housing frame means;

a plurality of winding pins slidably mounted in the cam housing frame means, and moveable with respect to the cam housing frame mean when engaged by the cam means;

gear means mounted to the cam means and shaft for rotating the cam means;

package support means mounted to the cam housing frame means for receiving a suture package, wherein said suture package comprises a winding channel for receiving a suture;

winding funnel means mounted to the package support means; and, means mounted to the package support means for aligning the winding funnel means with the package support means.

2. The fixture of claim 1 wherein the cam housing frame means comprises a frame having a top, a bottom and a pair of opposed sides, and further having a central opening for receiving the pivot shaft, and first and second cavities for receiving the cam means on each side of the central opening.

3. The fixture of claim 2 wherein the cam means comprises a first cam shaft and at least one cam fixedly mounted to said first cam shaft, the first cam shaft rotatably mounted to the frame in the first cavity of the frame, and a second cam shaft and at least one cam fixedly mounted to the second cam shaft, said second cam shaft rotatably mounted to the frame in the second cavity of the frame, wherein said first and second cam shafts each have an inner end extending into the central opening of the frame.

4. The fixture of claim 3 wherein the gear means comprises first and second bevel gears mounted to the inner ends of the first and second cam shafts, respectively, and a pinion gear mounted to the top of the pivot shaft such that the pinion gear engages the first and second bevel gears.

5. The fixture of claim 4 wherein the winding pins are mounted to a set of concentric cage nested plate members, said set of concentric nested cage plate members comprising a plurality members, cage plate members, said cage plate members comprising nested, concentric oval shaped rings, having tops and bottoms, moveable independent of each other in response to movement of the cam means to a first extended position and a second resting position, the pins mounted to the tops of the cage plate members, said cage plate members resting on top of the frame, wherein the set of cage plate members is centrally mounted on top of the cam frame housing.

6. The fixture of claim 5 wherein the cam means additionally comprises a cam follower for each of said at least one cam, each said cam follower mounted in a slot extending through the top of the frame and moveable vertically through said slot, each said cam follower having a bottom which engages a cam surface and a top which engages the bottom of one of said plurality of nested cage plate members.

7. The fixture of claim 6 wherein the package support means comprises a support plate for receiving a suture package having a suture winding channel, said support plate having a top and a bottom, said plate mounted over the top of the frame thereby forming a cavity between the bottom of the plate and the top of the frame, said plate having a plurality of winding pin holes extending therethrough for receiving winding pins, said plate having at least one alignment pin mounted to the top thereof.

8. The fixture of claim 7 wherein the winding funnel means comprises a member having a plurality of winding pin holes therethrough for receiving winding pins, and having at least one alignment pin cavity for receiving an alignment pin, said member having a top and a bottom, and a beveled winding surface for engaging a suture extending from said bottom.

9. The fixture of claim 6 wherein each of said at least one cam comprises a dwell section and an engagement section.

10. The fixture of claim 5 comprising biasing means mounted to the top of the frame and engaging the cage plate members, said biasing means exerting a downward bias on the cage plates members.

11. A method of winding a surgical suture into a surgical suture package having a grooved winding channel, said method comprising:

A) mounting a suture package to a winding fixture, wherein the suture package comprises an oval package having a top and a bottom, and a suture winding channel on the top for receiving a surgical suture, and wherein said winding fixture comprises:

a base plate having a top and a bottom;

a pivot shaft fixedly mounted to the top of the base plate;

a cam housing frame means rotatably mounted to the shaft;

cam means rotatably mounted in said cam housing frame means;

a plurality of winding pins slidably mounted in the cam housing frame means, and moveable with respect to the cam housing frame mean when engaged by the cam means;

gear means mounted to the cam means and shaft for rotating the cam means;

package support means mounted to the cam housing frame means for receiving a suture package, wherein said suture package comprises a winding channel for receiving a suture;

winding funnel means mounted to the package support means; and, means mounted to the package support means for aligning the winding funnel means with the package support means, B) mounting a first end of a surgical suture to the package; and, C) rotating the fixture a sufficient number of times to effectively wind the entire suture into the winding channel such that the suture is wound into a series of concentric coils.

* * * * *